United States Patent [19]

Hosono et al.

[11] Patent Number: 5,688,818
[45] Date of Patent: Nov. 18, 1997

[54] SUCCINAMIC ACID COMPOUND, PRODUCTION METHOD THEREOF AND USE THEREOF

[75] Inventors: Hiroshi Hosono, Ubaraki; Toshiyuki Nishio, Kawasaki; Hiromichi Ishikawa, Kobe; Yoshiyuki Nakamura, Shizuoka; Tetsuo Matsui, Tsukuba, all of Japan

[73] Assignees: Senju Pharmaceutical Co., Ltd.; The Green Cross Corporation, both of Osaka, Japan

[21] Appl. No.: 617,824

[22] PCT Filed: Aug. 1, 1994

[86] PCT No.: PCT/JP94/01266

§ 371 Date: Mar. 14, 1996

§ 102(e) Date: Mar. 14, 1996

[87] PCT Pub. No.: WO95/07898

PCT Pub. Date: Mar. 23, 1995

[30] Foreign Application Priority Data

Sep. 14, 1993 [JP] Japan .................... 5-250925

[51] Int. Cl.$^6$ .................... C07D 277/62; C07D 277/64
[52] U.S. Cl. .................... 514/367; 548/180
[58] Field of Search .................... 548/180; 514/367

[56] References Cited

U.S. PATENT DOCUMENTS

| 4,822,809 | 4/1989 | Summers et al. ............ 514/367 |
| 5,532,257 | 7/1996 | Hase et al. ................. 514/367 |

OTHER PUBLICATIONS

Katritzy et. al., "A Novel Synthesis of Benzothiazoles.", Synth. Commun., vol. 18, No. 7 (1988), pp. 651–658.
Minisci et. al., "Amidomethylation of Basic Heterocyclic . . . ", Chemical Abstract, vol. 84 (1976), p. 501, ABS#59237v.
Francesco et al., Chemical Abstract, vol. 84, 1976, p. 59237.

*Primary Examiner*—Matthew V. Grumbling
*Assistant Examiner*—Tamthom T. Ngo
*Attorney, Agent, or Firm*—Sughrue,Mion,Zinn,Macpeak & Seas, PLLC

[57] ABSTRACT

Provision of a succinamic acid compound of the formula (1)

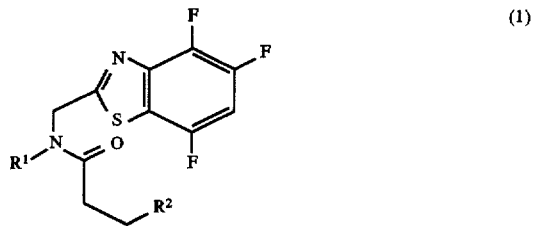

wherein $R^1$ is an alkyl or a lower alkenyl and $R^2$ is an optionally esterified carboxyl, a pharmaceutically acceptable salt thereof, an agent for the prophylaxis and/or treatment of the complications of diabetes, comprising, as an active ingredient, the succinamic acid compound or a pharmaceutically acceptable salt thereof, an aldose reductase inhibitor comprising, as an active ingredient, the succinamic acid compound or a pharmaceutically acceptable salt thereof, and a method for producing the succinamic acid compound or a pharmaceutically acceptable salt thereof. The novel succinamic acid compounds of the formula (1) of the present invention and pharmaceutically acceptable salts thereof have a strong aldose reductase activity-inhibitory in mammals such as human, and show superior safety. Hence, they are useful as pharmaceutical agents for the treatment of the complications of diabetes such as faulty union of corneal injury, cataract, neurosis, retinopathy and nephropathy, in particular, cataract and neurosis. According to the production method of the present invention, efficient production of such useful compounds of the present invention can be provided.

9 Claims, No Drawings

SUCCINAMIC ACID COMPOUND, PRODUCTION METHOD THEREOF AND USE THEREOF

This is a 371 of PCT/JP 94/01266 (Aug. 1, 1994).

TECHNICAL FIELD

The present invention relates to novel succinamic acid compounds having superior aldose reductase activity-inhibitory action, pharmaceutically acceptable salts thereof (hereinafter also generally referred to as the compound of the present invention), production thereof and pharmaceutical compositions containing the compound of the present invention.

The above-mentioned compound of the present invention is useful as an aldose reductase inhibitor and as an agent for the prophylaxis and/or treatment of the complications of diabetes, such as faulty union of corneal injury, diabetic cataract, retinopathy, nephropathy and neurosis.

1. Background Art

There have been conventionally known many compounds having an aldose reductase activity-inhibitory action and some of them have been found to be useful as pharmaceuticals. However, the succinamic acid compound of the formula (1) of the present invention has not been known. The present invention has been made in an attempt to develop a more superior pharmaceutical product.

2. Disclosure of the Invention

In view of the present situation, the present inventors have conducted intensive studies for the purpose of developing a therapeutic agent for the complications of diabetes, which has an aldose reductase activity-inhibitory action, and found that a certain succinamic acid compound can accomplish the object, which resulted in the completion of the present invention.

That is, the present invention relates to succinamic acid compounds of the following formula (1)

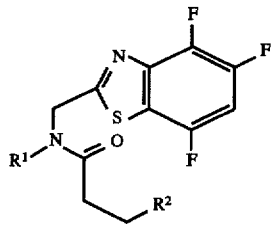

wherein $R^1$ is an alkyl or a lower alkenyl and $R^2$ is an optionally esterified carboxyl, pharmaceutically acceptable salts thereof, agents for the prophylaxis and/or treatment of the complications of diabetes which contain said succinamic acid compound or a pharmaceutically acceptable salt thereof as an active ingredient, and aldose reductase inhibitors containing, as an active ingredient, said succinamic acid compound or a pharmaceutically acceptable salt thereof, methods for producing the above-mentioned compounds of the formula (1) and pharmaceutically acceptable salts thereof, which comprise reacting a compound of the formula (2)

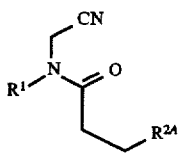

wherein $R^1$ is as defined above and $R^{2A}$ is an esterified carboxyl, or an acid addition salt thereof with 2-amino-3,4,6-trifluorothiophenol or an acid addition salt thereof, which is followed by, on demand, hydrolysis of said compound, and methods for producing the above-mentioned compounds of the formula (1) and pharmaceutically acceptable salts thereof, which comprise reacting a compound of the formula (3)

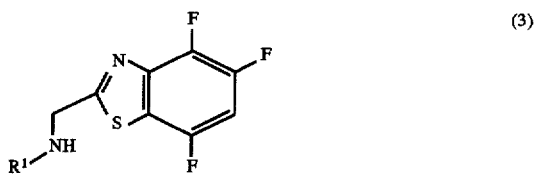

wherein $R^1$ is as defined above, with a compound of the formula (4)

wherein $R^{2A}$ is as defined above and X is a halogen atom, or an acid addition salt thereof, which is followed by, on demand, hydrolysis of said compound.

The compound of the present invention which is represented by the formula (1) above has a novel structure essentially including a succinamic acid moiety as a basic structure.

The respective terms used in the present specification are defined in the following.

In the above-mentioned formula (1), esterified carboxyl is exemplified by lower alkoxycarbonyl such as methoxycarbonyl, ethoxycarbonyl, propoxycarbonyl, isopropoxycarbonyl, butoxycarbonyl, isobutoxycarbonyl and tert-butoxycarbonyl, and aryloxycarbonyl and benzyloxycarbonyl both of which may have a substituent on the benzene ring, with preference given to ethoxycarbonyl.

Alkyl means linear, branched or cyclic alkyl having 1 to 16 carbon atoms, such as methyl, ethyl, propyl, isopropyl, cyclopropyl, cyclopropylmethyl, butyl, isobutyl, sec-butyl, tert-butyl, cyclobutyl, amyl, isoamyl, sec-amyl, tert-amyl, cyclopentyl, hexyl, heptyl, octyl, nonyl, decyl, undecyl, dodecyl, tridecyl, tetradecyl, pentadecyl and hexadecyl, with preference given to methyl, ethyl, propyl, isopropyl, cyclopropyl, cyclopropylmethyl, butyl, cyclobutyl, amyl, cyclopentyl, hexyl, cyclohexyl, octyl and hexadecyl.

Lower alkenyl means linear or branched alkenyl having 2 to 6 carbon atoms, such as vinyl, allyl, isopropenyl, 1-, 2- or 3-butenyl, and 1-, 2-, 3- or 4-pentenyl, 1-, 2-, 3-, 4- or 5-hexenyl, with preference given to allyl.

Halogen atom is exemplified by fluorine atom, chlorine atom, bromine atom and iodine atom. The pharmaceutically acceptable salt of the compound of the formula (1) includes, for example, alkali metal salts such as lithium, sodium and potassium, alkaline earth metal salts such as calcium, magnesium and berilium, aluminum salt, and organic salts such as triethylamine and pyridine.

The typical compounds of the formula (1) are, for example, the following compounds.

Ethyl N-(4,5,7-trifluorobenzothiazol-2-yl)methyl-N-methyl-succinamate
N-(4,5,7-Trifluorobenzothiazol-2-yl)methyl-N-methylsuccinamic acid
Ethyl N-(4,5,7-trifluorobenzothiazol-2-yl) methyl-N-ethylsuccinamate
N-(4,5,7-Trifluorobenzothiazol-2-yl) methyl-N-ethylsuccinamic acid
Ethyl N-(4,5,7-trifluorobenzothiazol-2-yl) methyl-N-propylsuccinamate
N-(4,5,7-Trifluorobenzothiazol-2-yl) methyl-N-propylsuccinamic acid
Ethyl N-(4,5,7-trifluorobenzothiazol-2-yl)methyl-N-isopropylsuccinamate
N-(4,5,7-Trifluorobenzothiazol-2-yl)methyl-N-isopropylsuccinamic acid
Ethyl N-(4,5,7-trifluorobenzothiazol-2-yl)methyl-N-butylsuccinamate
N-(4,5,7-Trifluorobenzothiazol-2-yl)methyl-N-butylsuccinamic acid
N-(4,5,7-Trifluorobenzothiazol-2-yl)methyl-N-isobutylsuccinamic acid
N-(4,5,7-Trifluorobenzothiazol-2-yl)methyl-N-sec-butylsuccinamic acid
N-(4,5,7-Trifluorobenzothiazol-2-yl)methyl-N-tert-butylsuccinamic acid
Ethyl N-(4,5,7-trifluorobenzothiazol-2-yl)methyl-N-amylsuccinamate
N-(4,5,7-Trifluorobenzothiazol-2-yl)methyl-N-amylsuccinamic acid
Ethyl N-(4,5,7-trifluorobenzothiazol-2-yl)methyl-N-hexylsuccinamate
N-(4,5,7-Trifluorobenzothiazol-2-yl)methyl-N-hexylsuccinamic acid
N-(4,5,7-Trifluorobenzothiazol-2-yl)methyl-N-heptylsuccinamic acid
Ethyl N-(4,5,7-trifluorobenzothiazol-2-yl)methyl-N-octylsuccinamate
N-(4,5,7-Trifluorobenzothiazol-2-yl)methyl-N-octylsuccinamic acid
N-(4,5,7-Trifluorobenzothiazol-2-yl)methyl-N-nonylsuccinamic acid
N-(4,5,7-Trifluorobenzothiazol-2-yl)methyl-N-decylsuccinamic acid
N-(4,5,7-Trifluorobenzothiazol-2-yl)methyl-N-undecylsuccinamic acid
Ethyl N-(4,5,7-trifluorobenzothiazol-2-yl)methyl-N-dodecylsuccinamate
N-(4,5,7-Trifluorobenzothiazol-2-yl)methyl-N-tridecylsuccinamic acid
Ethyl N-(4,5,7-trifluorobenzothiazol-2-yl)methyl-N-tetradecylsuccinamate
N-(4,5,7-Trifluorobenzothiazol-2-yl)methyl-N-pentadecylsuccinimic acid
Ethyl N-(4,5,7-trifluorobenzothiazol-2-yl)methyl-N-hexadecylsuccinamate
N-(4,5,7-Trifluorobenzothiazol-2-yl)methyl-N-hexadecylsuccinamic acid
Ethyl N-(4,5,7-trifluorobenzothiazol-2-yl)methyl-N-cyclopropylsuccinamate
N-(4,5,7-Trifluorobenzothiazol-2-yl)methyl-N-cyclopropylsuccinamic acid
Ethyl N-(4,5,7-trifluorobenzothiazol-2-yl)methyl-N-cyclobutylsuccinamate
N-(4,5,7-Trifluorobenzothiazol-2-yl)methyl-N-cyclobutylsuccinamic acid
Ethyl N-(4,5,7-trifluorobenzothiazol-2-yl)methyl-N-cyclopentylsuccinamate
N-(4,5,7-Trifluorobenzothiazol-2-yl)methyl-N-cyclopentylsuccinamic acid
Ethyl N-(4,5,7-trifluorobenzothiazol-2-yl)methyl-N-cyclohexylsuccinamate
N-(4,5,7-Trifluorobenzothiazol-2-yl)methyl-N-cyclohexylsuccinamic acid
N-(4,5,7-Trifluorobenzothiazol-2-yl)methyl-N-cycloheptylsuccinamic acid
N-(4,5,7-Trifluorobenzothiazol-2-yl)methyl-N-cyclooctylsuccinamic acid
N-(4,5,7-Trifluorobenzothiazol-2-yl)methyl-N-vinylsuccinamic acid
Ethyl N-(4,5,7-trifluorobenzothiazol-2-yl)methyl-N-allylsuccinamate
N-(4,5,7-Trifluorobenzothiazol-2-yl)methyl-N-allylsuccinamic acid
N-(4,5,7-Trifluorobenzothiazol-2-yl)methyl-N-isopropenylsuccinamic acid
N-(4,5,7-Trifluorobenzothiazol-2-yl)methyl-N-1-butenylsuccinamic acid
N-(4,5,7-Trifluorobenzothiazol-2-yl)methyl-N-2-butenylsuccinamic acid
N-(4,5,7-Trifluorobenzothiazol-2-yl)methyl-N-3-butenylsuccinamic acid
N-(4,5,7-Trifluorobenzothiazol-2-yl)methyl-N-1-pentenylsuccinamic acid
N-(4,5,7-Trifluorobenzothiazol-2-yl)methyl-N-2-pentenylsuccinamic acid
N-(4,5,7-Trifluorobenzothiazol-2-yl)methyl-N-3-pentenylsuccinamic acid
N-(4,5,7-Trifluorobenzothiazol-2-yl)methyl-N-4-pentenylsuccinamic acid
N-(4,5,7-Trifluorobenzothiazol-2-yl)methyl-N-1-hexenylsuccinamic acid
Ethyl N-(4,5,7-trifluorobenzothiazol-2-yl)methyl-N-2-hexenylsuccinamate
N-(4,5,7-Trifluorobenzothiazol-2-yl)methyl-N-3-hexenylsuccinamic acid
Ethyl N-(4,5,7-trifluorobenzothiazol-2-yl)methyl-N-4-hexenylsuccinamate
N-(4,5,7-Trifluorobenzothiazol-2-yl)methyl-N-5-hexenylsuccinamic acid The compound of the formula (1) of the present invention can be produced by various methods, and the typical methods for producing the compound are explained in detail in the following.

Production 1

The compound of the formula (1) of the present invention can be produced by reacting a compound of the formula (2)

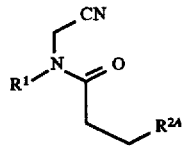 (2)

wherein $R^1$ is alkyl or lower alkenyl and $R^{2A}$ is esterified carboxyl, or an acid addition salt thereof with 2-amino-3,4,6-trifluorothiophenol or an acid addition salt thereof under an inert gas atmosphere, which is followed by, on demand, hydrolysis in the presence of a base or acid.

When the compound of the formula (2) and 2-amino-3,4,6-trifluorothiophenol are not acid addition salts when added to each other, the reaction needs to be carried out in the presence of a strong acid.

Particularly preferable solvents to be used for the above-mentioned reactions include, for example, methanol, ethanol and propanol. In this case, the reaction temperature is preferably from 60° C. to refluxing temperature.

When the solvent is not used, the compound of the formula (2) and an acid addition salt (e.g., hydrochloride) of 2-amino-3,4,6-trifluorothiophenol may be subjected to eutectic reaction at 130°–180° C. As the inert gas, usable are, for example, nitrogen and argon.

Examples of the suitable base to be used for hydrolysis include alkali metal hydroxides such as sodium hydroxide and potassium hydroxide, and alkali metal carbonates such as sodium carbonate and potassium carbonate. Examples of the suitable acid include organic acids such as formic acid, acetic acid, propionic acid, trifluoroacetic acid, benzenesulfonic acid and p-toluenesulfonic acid, and inorganic acids such as hydrochloric acid, hydrobromic acid, sulfuric acid and phosphoric acid.

This reaction is generally carried out in a conventional solvent which does not exert adverse influence on the reaction, such as water, acetone, dioxane, dichloromethane, methanol, ethanol, propanol, pyridine and N,N-dimethylformamide, or a mixture thereof. When the base or acid to be used in this reaction is liquid, it my be used as a solvent.

The reaction temperature is not particularly limited, and the reaction is carried out at a temperature of from under cooling to under heating.

Production 2

The compound of the formula (1) of the present invention can be produced by reacting a compound of the formula (3)

wherein $R^1$ is as defined above, with a compound of the formula (4)

wherein $R^{24}$ is as defined above and X is a halogen atom, or an acid addition salt thereof under the basic conditions and/or under an inert gas atmosphere as necessary, which is followed by, on demand, hydrolysis in the presence of a base or acid.

The base to be used to provide the above-mentioned basic conditions includes, for example, inorganic bases and organic bases such as alkali metal hydrides (e.g., sodium hydride), alkaline earth metal hydrides (e.g., calcium hydride), alkali metal hydroxides (e.g., sodium hydroxide and potassium hydroxide), alkali metal carbonates (e.g., sodium carbonate and potassium carbonate), alkali metal hydrogencarbonates (e.g., sodium hydrogencarbonate and potassium hydrogencarbonate), alkali metal alkoxides (e.g., sodium methoxide, sodium ethoxide and potassium tert-butoxide), alkali metal salts of alkanoic acid (e.g., sodium acetate), trialkylamines (e.g., triethylamine), pyridine compounds (e.g., pyridine, lutidine, picoline and 4-dimethylaminopyridine), and quinoline. Examples of the inert gas include nitrogen, argon and helium.

The above-mentioned reaction is generally carried out in various solvents such as conventional solvents which do not exert adverse influence on the reaction (e.g., dichloromethane, chloroform, 1,2-dichloroethane, 1,2-dimethoxyethane, tetrahydrofuran, benzene and toluene) or a mixture thereof. Particularly preferable solvents are dichloromethane, chloroform and tetrahydrofuran.

The reaction temperature is not particularly limited, and the reaction is carried out in a wide temperature range of from under cooling to under heating. The compound of the present invention thus produced is isolated and purified as necessary by conventional methods such as extraction, precipitation, fractional chromatography, fractionation, crystallization and recrystallization. The compound of the present invention can be converted to pharmaceutically acceptable salts on demand by a conventional method.

The starting compound of the formula (2) shown in the aforementioned Production 1 is a novel compound and can be produced, for example, by the following method.

A compound of the above-mentioned formula (4) and a compound of the formula (5)

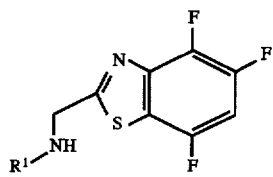

wherein $R^1$ is as defined above, or a salt thereof are reacted under the same reaction conditions as in Production 2.

The starting compound of the formula (5) is a known substance or can be easily produced by a known method [O. Kirino et al., Agric. Biol. Chem., 44, 25–30 (1980)].

The starting compound of the formula (3) shown in the aforementioned Production 1 is also a novel compound and can be produced, for example, by the following method.

A compound of the formula (5) or an acid addition salt thereof and 2-amino-3,4,6-trifluorothiophenol or an acid addition salt thereof are reacted under the same reaction conditions as in Production 1.

Of the succinamic acid compounds of the formula (1), typical compounds were subjected to pharmacological test to examine their effectiveness and the results are shown in the following. Note that the compounds of the present invention which are not exemplarily shown here also showed the similar effects.

1) Aldose reductase activity-inhibitory action

Preparation of enzyme

An aldose reductase enzyme standard product was prepared from swine lens according to the method of S. Hayman et al. [Journal of Biological Chemistry, 240, 877–882 (1965)]. That is, swine lenses freeze-stored at –80° C. were homogenized with distilled water and centrifuged at 10,000 G for 15 minutes. The supernatant was prepared into a 40% ammonium sulfate solution and subjected to centrifugation at 10,000 G for 10 minutes. The supernatant obtained was dialyzed overnight against a 0.05M sodium chloride solution to give a dialyzed solution, which was used as an enzyme standard product.

Activity determination

The activity of aldose reductase was determined by the above-mentioned method of S. Hayman et al. That is, the above-mentioned enzyme solution (25 μl) and a drug solution (25 μl) dissolved in 1% DMSO at various concentrations were added to a 40 mM phosphate buffer (200 μl, pH 6.2) containing, at final concentrations, 0.4M lithium sulfate, 0.1 mM NADPH (reduced type nicotinamide adenine dinucleotide phosphate) and 3 mM dl-glyceraldehyde as a substrate. The mixture was allowed to react at 25° C. for 2 minutes and the changes in absorbance at 340 nm were determined with COBAS FARA II (manufactured by Roche).

The changes in absorbance when 1% DMSO was added instead of the drug solution was taken as 100%, based on which 50% inhibition concentration ($IC_{50}$) was calculated and shown in Table 1.

$IC_{50}$ (M) in the Table shows the concentration of the compound of the present invention at which the aldose reductase activity was inhibited by 50%. The test drug number indicates the example number to be mentioned later. EPALRESTAT is described in Japanese Patent Unexamined Publication No. 40478/1982.

TABLE 1

| Test compound | $IC_{50}$ (M) |
| --- | --- |
| Example 23 | $1.3 \times 10^{-8}$ |
| Example 26 | $1.8 \times 10^{-8}$ |
| Example 29 | $1.7 \times 10^{-8}$ |
| EPALRESTAT | $2.1 \times 10^{-8}$ |

2) Inhibitory action on sorbitol accumulation in tissues of rats with experimental diabetes Test Compounds: Compounds of Example 23 and 29 and EPALRESTAT (described in Japanese Patent Unexamined Publication No. 40478/1982)

Sprague-Dawley rats (male, 6 weeks old, 5–6 per group) were fasted for 18 hours and injected with streptozotocin (SIGMA, 60 mg/kg) via the tail vein under ether anesthesia to prepare rats with diabetes.

The test compounds were orally administered at 4, 8 and 24 hours after the injection of streptozotocin. EPALRESTAT was administered orally in the dose of 30 mg/kg and the compounds of Examples 23 and 29 were administered orally in the dose of 10 mg/kg as a 0. 5% carboxymethylcellulose suspension, respectively. During the administrations, the rats were raised under free access to feed and water and the sorbitol content in the tissues (erythrocytes, sciatic nerve, lens) was determined 3 hours after the final administration, according to the enzyme method of H. Y. Bergmeyer et al. [Methods of Enzymatic Analysis, vol. 3, 1323–1330 (1974)] with the use of SDH (sorbitol dehydrogenase) and NAD (β-nicotinamide adenine dinucleotide). The results are expressed in percent (%) relative to the value of a control group administered with a 0.5% carboxymethylcellutose solution (solvent) instead of the compound, which was taken as 100%. The results are shown in Table 2.

TABLE 2

| Test compound | Sorbitol accumulation (%) | | |
| --- | --- | --- | --- |
| (mg/kg) | erythrocytes | nerve | lens |
| Example 23 (10) | 6.3* | 4.2* | 69.5 |
| Example 29 (10) | 12.2* | 1.0* | 45.4* |
| EPALRESTAT (30) | 66.5 | 99.9 | 89.1 |

Tukey's Multiple Range Test: * $p < 0.01$

The acute toxicity (safety) of the single dose of the compound of the present invention was confirmed by the following test.

Normal ICR mice (male, 7 weeks old, 5 per group) were fasted for 18 hours and the compound (300 mg/kg) of Example 29 was orally administered as a 0.5% carboxymethylcellulose suspension. To the control group, a 0.5% carboxymethylcellulose solution alone was orally administered and observation was continued for 14 days thereafter, during which period the mice were allowed to take feed and water freely.

As a result, there was no death case among the mice administered with the compound of Example 29 and their weights showed transition in the same manner as in the control group.

As mentioned above, the compound of the present invention has a superior aldose reductase activity-inhibitory action on mammals inclusive of human, cow, horse, dog, mouse, rat and so on and shows superior safety. Accordingly, it is effectively used for the prevention and/or treatment of the complications of diabetes, such as faulty union of corneal injury, diabetic neurosis, nephropathy, retinopathy and cataract. When the compound of the present invention is administered for the prevention and/or treatment of the above-mentioned diseases, oral or parenteral administration can be employed.

A pharmaceutical composition containing the compound of the present invention is provided in the form of a solid preparation, semi-solid preparation or liquid preparation together with organic or inorganic carrier and/or excipient suitable for external, oral or local administration. The compound of the present invention is used for the provision of a suitable dosage form such as tablet, pellet, capsule, suppository, liquid, emulsion or suspension along with pharmacologically acceptable auxiliary ingredients.

The auxiliary ingredients include, for example, those effectively used for the production of solid, semi-solid or liquid preparations, such as water, glucose, lactose, gelatin, mannitol, starch paste, magnesium trisillicate, corn starch, keratin, colloidal silica, potato starch and urea. In addition, the auxiliary ingredients include stabilizers, extenders, colorings and aromatic agents. So as to retain the activity of the compound of the present invention, a preservative may be also contained. The pharmaceutical preparation should contain the compound of the present invention in an amount sufficient to produce the desired therapeutic effect against the progress or symptom of the target diseases.

When the compound of the present invention is administered to human, it is preferably administered, for example, parenterally as an injection or eye drop, or orally in an amount sufficient to inhibit aldose reductase activity or an amount sufficient to prevent and/or treat the complications of diabetes. While the dose of the compound of the present invention varies depending on age, body weight, symptom, therapeutic effect, administration route, administration period etc., the compound is generally administered orally in the dose of 1–2000 mg/day, preferably 10–600 mg/day in a single to three doses a day.

The pharmaceutical composition of the present invention contains the compound of the present invention. Hence, it is effective as an aldose reductase inhibitor or for the prophylaxis and/or treatment of the complications of diabetes, such as faulty union of corneal injury, diabetic neurosis, nephropathy, retinopathy and cataract, as mentioned above.

An administration of an effective amount of the compound of the present invention to mammals such as human leads to the inhibition of aldose reductase activity and enables prophylaxis and/or treatment of the complications of diabetes, such as faulty union of corneal injury, diabetic neurosis, nephropathy, retinopathy and cataract.

The present invention is explained in more detail in the following by way of examples, to which the present invention is not limited.

EXAMPLE 1

Production of ethyl N-(4,5,7-trifluorobonzothiazol-2-yl)methyl-N-propylsuccinamate Ethyl N-cyanomethyl-N-propylsuccinamate (249 mg) and 2-amino-3,4,6-trifluorothiophenol hydrochloride (250 mg) were added to anhydrous ethanol (3 ml) and the mixture was refluxed under heating under an argon atmosphere.

Seventeen hours later, the solvent was distilled away and water was added to the residue, which was followed by extraction with ethyl acetate.

The organic layer was washed with saturated brine and dried over anhydrous magnesium sulfate. The solvent was distilled away and the obtained oily substance was subjected to silica gel column chromatography and eluted with hexane-ethyl acetate to give 168 mg of the title compound. The properties of this compound are shown below.

MS (EI, m/z): 388 (M$^+$)

NMR (CDCl$_3$, δ):

0.94 (3H, t), 1.27 (3H, t), 1.53–1.73 (2H, m), 2.70–2.77 (4H, m), 3.42 (2H, t), 4.17 (2H, q), 4.94 (2H, s), 6.98–7.07 (1H, m)

In the following examples, the following compounds (Examples 2–15) were obtained substantially in the same manner as in Example 1.

EXAMPLE 2

Ethyl N-(4,5,7-trifluorobenzothiazol-2-yl)methyl-N-amylsuccinamate

ME (EI, m/z): 416 (M$^+$)

NMR (CDCl$_3$, δ):

0.88 (3H, t), 1.26–1.32 (4H, m), 1.27 (3H, t), 1.63–1.68 (2H, m), 2.69–2.74 (4H, m), 3.44 (2H, t), 4.17 (2H, q), 4.94 (2H, s), 6.98–7.07 (1H, m)

EXAMPLE 3

Ethyl N-(4,5,7-trifluorobenzothiazol-2-yl)methyl-N-hexylsuccinamate

ME (EI, m/z): 430 (M$^+$)

NMR (CDCl$_3$, δ):

0.87 (3H, t), 1.27 (3H, t), 1.29 (6H, m), 1.65 (2H, m), 2.69–2.74 (4H, m), 3.44 (2H, t), 4.17 (2H, q), 4.94 (2H, s), 6.98–7.07 (1H, m)

EXAMPLE 4

Ethyl N-(4,5,7-trifluorobenzothiazol-2-yl)methyl-N-hexadecylsuccinamate

ME (EI, m/z): 570 (M$^+$)

M (CDCl$_3$, δ):

0.88 (3H, t), 1.25 (26H, m), 1.27 (3H, t), 1.64 (2H, m), 2.69–2.74 (4H, m), 3.44 (2H, t), 4.17 (2H, q), 4.94 (2H, s), 6.98–7.07 (1H, m)

EXAMPLE 5

Ethyl N-(4,5,7-trifluorobenzothiazol-2-yl)methyl-N-cyclopropylmethylsuccinamate

ME (EI, m/z): 400 (M$^+$)

NMR (CDCl$_3$, δ):

0.26–0.32 (2H, m), 0.43–0.61 (2H, m), 0.97–1.07 (1H, m), 1.27 (3H, t), 2.76 (2H, s), 3.38 (2H, d), 4.17 (2H, q), 5.07 (2H, s), 6.98–7.07 (1H, m)

EXAMPLE 6

Ethyl N-(4,5,7-trifluorobenzothiazol-2-yl)methyl-N-cyclobutylsuccinamate

MS (EI, m/z): 400 (M$^+$)

NMR (CDCl$_3$, δ):

1.27 (3H, t), 1.57–1.77 (2H, m), 2.21–2.31 (4H, m), 2.74 (4H, s), 4.17 (2H, q), 4.47 (1H, m), 5.05 (2H, s), 6.97–7.06 (1H, m)

EXAMPLE 7

Ethyl N-(4,5,7-trifluorobenzothiazol-2-yl)methyl-N-cyclopentylsuccinamate

MS (EI, m/z): 414 (M$^+$)

NMR (CDC$_3$, δ):

1.28 (3H, t), 1.60–1.91 (8H, m), 2.73–2.82 (4H, m), 4.17 (2H, q), 4.33 (1H, m), 4.88 (2H, s), 6.96–7.05 (1H, m)

EXAMPLE 8

Ethyl N-(4,5,7-trifluorobenzothiazol-2-yl)methyl-N-methylsuccinamate

MS (CI, m/z): 361 (MH$^+$)

NMR (CDCl$_3$, δ):

1.28 (3H, t), 2.73 (4H, s), 3.20 (3H, s), 4.17 (2H, q), 4.98 (2H, s), 6.99–7.09 (1H, m)

EXAMPLE 9

Ethyl N-(4,5,7-trifluorobenzothiazol-2-yl)methyl-N-ethylsuccinamate

MS (CI, m/z): 375 (MH$^+$)

NMR (CDCl$_3$, δ):

1.15–1.35 (6H, m), 2.63–2.80 (4H, m), 3.55 (2H, q), 4.17 (2H, q), 4.94 (2H, s), 6.98–7.09 (1H, m)

EXAMPLE 10

Ethyl N-(4,5,7-trifluorobenzothiazol-2-yl)methyl-N-isopropylsuccinamate

MS (CI, m/z): 389 (MH$^+$)

NMR (CDCl$_3$, δ):

1.23–1.33 (9H, m), 2.74–2.83 (4H, m), 4.17 (2H, q), 4.29 (1H, m), 4.90 (2H, s), 6.95–7.09 (1H, m)

EXAMPLE 11

Ethyl N-(4,5,7-trifluorobenzothiazol-2-yl)methyl-N-butylsuccinamate

MS (CI, m/z): 403 (MH$^+$)

NMR (CDCl$_3$, δ):

0.94 (3H, t), 1.22–1.43 (5H, m), 1.56–1.72 (2H, m), 2.67–2.80 (4H, m), 3.45 (2H, t), 4.17 (2H, q), 4.94 (2H, s), 6.97–7.08 (1H, m)

EXAMPLE 12

Ethyl N-(4,5,7-trifluorobenzothiazol-2-yl)methyl-N-octylsuccinamate

MS (CI, m/z): 459 (MH$^+$)

NMR (CDCl$_3$, δ):

0.87(3H, t), 1.17–1.35 (13H, m), 1.54–1.73 (2H, m), 2.67–2.80 (4H, m), 3.39–3.49 (2H, dd), 4.17 (2H, q), 4.95 (2H, s), 6.98–7.08 (1H, m)

EXAMPLE 13

Ethyl N-(4,5,7-trifluorobenzothiazol-2-yl)methyl-N-allylsuccinamate

MS (CI, m/z): 387 (MH$^+$)

NMR (CDCl$_3$, δ):

1.27 (3H, t), 2.72 (4H, s), 4.08–4.22 (4H, m), 4.95 (2H, s), 5.20–5.33 (2H, m), 5.83 (1H, m), 6.96–7.06 (1H, m)

EXAMPLE 14

Ethyl N-(4,5,7-trifluorobenzothiazol-2-yl)methyl-N-cyclopropylsuccinamate

MS (CI, m/z): 387 (MH$^+$)

NMR (CDCl$_3$, δ):
0.91–1.02 (4H, m), 1.27 (3H, t), 2.74 (2H, dd), 2.87–2.99 (3H, m), 4.17 (2H, q), 5.00 (2H, s), 6.97–7.07 (1H, m)

EXAMPLE 15

Ethyl N-(4,5,7-trifluorobenzothiazol-2-yl)methyl-N-cyclohexylsuccinamate

MS (CI, m/z): 429 (MH$^+$)

NMR (CDCl$_3$, δ):
1.09–1.91 (13H, m), 2.77 (4H, s), 3.77 (1H, m), 4.17 (2H, q), 4.92 (2H, s), 6.96–7.06 (1H, m)

EXAMPLE 16

Production of N-(4,5,7-trifluorobenzothiazol-2-yl)methyl-N-propylsuccinamic acid The compound (162 mg) of Example 1 was dissolved in a solution of methanol-dioxane (1:2, v/v, 3 ml) and 0.5N sodium hydroxide solution (1.00 ml) was dropwise added while stirring under ice-cooling, which was followed by stirring fop 1.5 hours. The mixture was diluted with water and made to assume acidity with 10% hydrochloric acid. The mixture was extracted with dichloromethane.

The organic layer was washed with saturated brine and dried over anhydrous magnesium sulfate. The solvent was distilled away. Isopropyl ether and hexane were added to the residue to allow crystallization to give 119 mg of the title compound. The properties of this compound are shown below.

MS (EI, m/z): 360 (M$^+$)

IR (KBr, cm$^{-1}$): 2900–3200, 1740, 1720, 1620

NMR (CDCl$_3$, δ):
0.94 (3H, t), 1.65–1.75 (2H, m), 2.74–2.83 (4H, m), 3.42 (2H, t), 4.96 (2H, s), 6.98–7.07 (1H, m)

In the following examples, the following compounds (Examples 17–30) were obtained substantially in the same manner as in Example 16.

EXAMPLE 17

N-(4,5,7-Trifluorobenzothiazol-2-yl)methyl-N-amylsuccinamic acid

MS (EI, m/z): 388 (M$^+$)

IR (KBr, cm$^{-1}$): 2620–3080, 1710, 1650

NMR (CDCl$_3$, δ):
0.88 (3H, t), 1.26–1.31 (4H, m), 1.62–1.68 (2H, m), 2.73–2.83 (4H, m), 3.44 (2H, t), 4.95 (2H, s), 6.98–7.07 (1H, m)

EXAMPLE 18

N-(4,5,7-Trifluorobenzothiazol-2-yl)methyl-N-hexylsuccinamic acid

MS (EI, m/z): 402 (M$^+$)

IR (KBr, cm$^{-1}$): 2630–3090, 1710, 1660

NMR (CDCl$_3$, δ):
0.86 (3H, t), 1.28 (6H, m), 1.6q (2H, m), 2.69–2.14 (4H, m), 3.44 (2H, t), 4.94 (2H, s), 6.98–7.07 (1H, m)

EXAMPLE 19

N-(4,5,7-Trifluorobenzothiazol-2-yl)methyl-N-hexadecylsuccinamic acid

MS (EI, m/z): 542 (M$^+$)

IR (KBr, cm$^{-1}$): 2610–3090, 1710, 1650

NMR (CDCl$_3$, δ):
0.88 (3H, t), 1.25 (26H, m), 1.63 (2H, m), 2.73–2.80 (4H, m), 3.43 (2H, t), 4.94 (2H, s), 6.98–7.07 (1H, m)

EXAMPLE 20

N-(4,5,7-Trifluorobenzothiazol-2-yl)methyl-N-cyclopropylmethylsuccinamic acid

MS (EI, m/z): 372 (M$^+$)

IR (KBP, cm$^{-1}$): 2960–3170, 1740, 1720, 1620

NMR (CDCl$_3$, δ):
0.26–0.31 (2H, m), 0.54–0.61 (2H, m), 0.96–1.05 (1H, m), 2.80 (2H, s), 3.38 (2H, d), 5.08 (2H, s), 6.98–7.07 (1H, m)

EXAMPLE 21

N-(4,5,7-Trifluorobenzothiazol-2-yl)methyl-N-cyclobutylsuccinamic acid

MS (EI, m/z): 372 (M$^+$)

IR (KBr, cm$^{-1}$): 2980–3170, 1740, 1720, 1610

NMR (CDCl$_3$, δ):
1.62–1.78 (2H, m), 2.21–2.32 (4H, m), 2.77 (4H, s), 4.44 (1H, m), 5.06 (2H, s), 6.97–7.06 (1H, m)

EXAMPLE 22

N-(4,5,7-Trifluorobenzothiazol-2-yl)methyl-N-cyclopentylsuccinamic acid

MS (EI, m/z): 386 (M$^+$)

IR (KBr, cm$^{-1}$): 2600–3170, 1710, 1650

NMR (CDCl$_3$, δ):
1.63–1.90 (8H, m), 2.82 (4H, s), 4.31 (1H, m), 4.89 (2H, s), 6.96–7.05 (1H, m)

EXAMPLE 23

N-(4,5,7-Trifluorobenzothiazol-2-yl)methyl-N-methylsuccinamic acid

MS (CI, m/z): 333 (MH$^+$)

IR (KBr, cm$^{-1}$): 2900–3200, 1740, 1720, 1630

NMR (CDCl$_3$, δ):
2.75 (4H, s), 3.21 (3H, s), 4.98 (2H, s), 6.97–7.12 (1H, m)

EXAMPLE 24

N-(4,5,7-Trifluorobenzothiazol-2-yl)methyl-N-ethylsuccinamic acid

MS (CI, m/z): 347 (MH$^+$)

IR (KBr, cm$^{-1}$): 2920–3220, 1740, 1720, 1630

NMR (CDCl$_3$, δ):

1.26 (3H, t), 2.70–2.85 (4H, m), 3.54 (2H, q), 4.95 (2H, s), 6.98–7.09 (1H, m)

EXAMPLE 25

N-(4,5,7-Trifluorobenzothiazol-2-yl)methyl-N-isopropylsuccinamic acid

MS (CI, m/z): 361 (MH$^+$)

IR (KBr, cm$^{-1}$): 2620–3510, 1720, 1610

NMR (CDCl$_3$, δ):

1.27 (3H, t), 1.29 (3H, t), 2.80 (4H, s), 4.27 (1H, m), 4.92 (2H, s), 6.95–7.07 (1H, m)

EXAMPLE 26

N-(4,5,7-Trifluorobenzothiazol-2-yl)methyl-N-butylsuccinamic acid

MS (CI, m/z): 375 (MH$^+$)

IR (KBr, cm$^{-1}$): 2620–3070, 1710, 1660

NMR (CDCl$_3$, δ):

0.93 (3H, t), 1.24–1.43 (2H, m), 1.54–1.70 (2H, m), 2.68–2.85 (4H, m), 3.44 (2H, t), 4.95 (2H, s), 6.95–7.08 (1H, m)

EXAMPLE 27

N-(4,5,7-Trifluorobenzothiazol-2-yl)methyl-N-octylsuccinamic acid

MS (CI, m/z): 431 (MH$^+$)

IR (KBr, cm$^{-1}$): 2600–3100, 1710, 1640

NMR (CDCl$_3$, δ):

0.87 (3H, t), 1.15–1.35 (10H, m), 1.52–1.72 (2H, m), 2.68–2.83 (4H, m) 3.38–3.48 (2H, dd), 4.95 (2H, s), 6.98–7.08 (1H, m)

EXAMPLE 28

N-(4,5,7-Trifluorobenzothiazol-2-yl)methyl-N-allylsuccinamic acid

MS (CI, m/z): 359 (MH$^+$)

IR (KBr, cm$^{-1}$): 2950–3200, 1740, 1630

NMR (CDCl$_3$, δ):

2.68–2.83 (4H, m), 4.08–4.15 (4H, m), 4.95 (2H, s), 5.19–5.33 (2H, m), 5.83 (1H, m), 7.02–7.12 (1H, m)

EXAMPLE 29

Ethyl N-(4,5,7-trifluorobenzothiazol-2-yl)methyl-N-cyclopropylsuccinamate

MS (CI, m/z): 359 (MH$^+$)

IR (KBr, cm$^{-1}$): 2980–3230, 1740, 1730, 1640

NMR (CDCl$_3$, δ):

0.89–1.07 (4H, m), 2.79 (2H, dd), 2.85–3.00 (3H, m), 5.00 (2H, s), 6.98–7.08 (1H, m)

EXAMPLE 30

N-(4,5,7-Trifluorobenzothiazol-2-yl)methyl-N-cyclohexylsuccinamic acid

MS (CI, m/z): 401 (MH$^+$)

IR (KBr, cm$^{-1}$): 2600–3080, 1710, 1640

NMR (CDCl$_3$, δ):

1.10–1.91 (10H, m), 2.80 (4H, s), 3.74 (1H, m), 4.94 (2H, s), 6.96–7.06 (1H, m)

Examples of the preparations of the present invention containing the compound of the present invention as an active ingredient are shown in the following.

FORMULATION EXAMPLE 1

| | |
|---|---|
| Compound of Example 9 | 20 g |
| Lactose | 315 g |
| Corn starch | 125 g |
| Crystalline cellulose | 25 g |

The above ingredients were homogeneously mixed and an aqueous solution (200 ml) of 7.5% hydroxypropylcellulose was added. The mixture was prepared into granules by an extrusion granulator with the use of a 0.5 m diameter screen. The granules were immediately Pounded and dried. The dry granules were coated with a film coating solution (1.9 kg) of the following composition by a fluid-type granulator to give enteric granules.

Coating Solution

| | | |
|---|---|---|
| Hydroxypropylmethylcellulose phthalate | 5.0 | (w/w) % |
| Stearic acid | 0.25 | (w/w) % |
| Methylene chloride | 50.0 | (w/w) % |
| Ethanol | 44.75 | (w/w) % |

FORMULATION EXAMPLE 2

| | |
|---|---|
| Compound of Example 6 | 20 g |
| Lactose | 100 g |
| Corn starch | 36 g |
| Crystalline cellulose | 30 g |
| Calcium carboxymethylcellulose | 10 g |
| Magnesium stearate | 4 g |

The above ingredients were homogeneously mixed and prepared by a single punch tableting machine into tablets each weighing 200 mg with the use of a 7.5 mm diameter punch. Then, the film coating solution of the following composition was spray-coated at 10 mg per tablet to give enteric coated tablets.

Coating Solution

| | | |
|---|---|---|
| Hydroxypropylmethylcellulose phthalate | 8.0 | (w/w) % |
| Glycerol fatty acid ester | 0.4 | (w/w) % |
| Methylene chloride | 50.0 | (w/w) % |
| White beewax | 0.1 | (w/w) % |
| Isopropanol | 41.5 | (w/w) % |

FORMULATION EXAMPLE 3

| | |
|---|---|
| Compound of Example 23 | 200 g |
| Polysorbate 80 | 20 g |
| PANASETO ® 810 | 1780 g |

The above ingredients were mixed and completely dissolved. With the use of a film solution for soft capsules composed of gelatin (100 parts), con. glycerine (30 parts), ethyl p-hydroxybenzoate (0.4 part) and propyl p-hydroxybenzoate (0.2 part), soft capsules containing 200 mg of a drug solution per capsule were prepared by a rotary method.

FORMULATION EXAMPLE 4

| Compound of Example 26 | 100 mg |
| --- | --- |
| Sodium acetate | 2 mg |
| Acetic acid (for adjusting to pH 5.8) | suitable amount |
| Distilled water | remaining amount |
| Total | 10 ml/vial |

An injection having the above formulation was prepared by a conventional method.

FORMULATION EXAMPLE 5

| Compound of Example 29 | 0.05 g |
| --- | --- |
| Polysorbate 80 | 0.2 g |
| Sodium hydrogenphosphate 2 hydrate | 0.2 g |
| Disodium hydrogenphosphate 12 hydrate | 0.5 g |
| Sodium chloride | 0.75 g |
| Methyl p-hydroxybenzoate | 0.026 g |
| Propyl p-hydroxybenzoate | 0.014 g |
| Sterile purified water | suitable amount |
| Total | 100 ml |

An eye drop having the above formulation was prepared by a conventional method.

Industrial Applicability

The novel succinamic acid compounds of the formula (1) of the present invention and pharmaceutically acceptable salts thereof have an aldose reductase activity-inhibitory action in mammals such as human, and show superior safety. Hence, they are useful as pharmaceutical agents for the treatment of the complications of diabetes such as faulty union of corneal injury, cataract, neurosis, retinopathy and nephropathy, in particular, cataract and neurosis.

According to the production method of the present invention, efficient production of such useful compounds of the present invention can be provided.

What is claimed is:

1. A succinamic acid compound of the following formula (1)

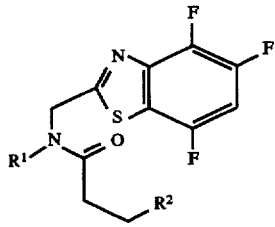

wherein $R^1$ is linear branched or cyclic alkyl or a lower alkenyl and $R^2$ is an optionally esterified carboxyl, or a pharmaceutically acceptable salt thereof.

2. The succinamic acid compound of claim 1 wherein $R^2$ in the formula (1) is ethoxycarbonyl, or a pharmaceutically acceptable salt thereof.

3. The succinamic acid compound of claim 1 wherein $R^1$ in the formula (1) is methyl, cyclopropyl or butyl, or a pharmaceutically acceptable salt thereof.

4. The succinamic acid compound of claim 1, which is a member selected from the group consisting of Ethyl N-(4,5,7-trifluorobenzothiazol-2-yl)methyl-N-propylsuccinamate;
Ethyl N-(4,5,7-trifluorobenzothiazol-2-yl)methyl-N-amylsuccinamate;
Ethyl N-(4,5,7-trifluorobenzothiazol-2-yl)methyl-N-hexylsuccinamate;
Ethyl N-(4,5,7-trifluorobenzothiazol-2-yl)methyl-N-hexadecylsuccinamate;
Ethyl N-(4,5,7-trifluorobenzothiazol-2-yl)methyl-N-cyclopropylmethylsuccinamate;
Ethyl N-(4,5,7-trifluorobenzothiazol-2-yl)methyl-N-cyclobutysuccinamate;
Ethyl N-(4,5,7-trifluorobenzothiazol-2-yl)methyl-N-cyclopentylsuccinamate;
Ethyl N-(4,5,7-trifluorobenzothiazol-2-yl)methyl-N-methylsuccinamate;
Ethyl N-(4,5,7-trifluorobenzothiazol-2-yl)methyl-N-ethylsuccinamate;
Ethyl N-(4,5,7-trifluorobenzothiazol-2-yl)methyl-N-isopropylsuccinamate;
Ethyl N-(4,5,7-trifluorobenzothiazol-2-yl)methyl-N-butylsuccinamate;
Ethyl N-(4,5,7-trifluorobenzothiazol-2-yl)methyl-N-octylsuccinamate;
Ethyl N-(4,5,7-trifluorobenzothiazol-2-yl)methyl-N-allylsuccinamate;
Ethyl N-(4,5,7-trifluorobenzothiazol-2-yl)methyl-N-cyclopropylsuccinamate;
Ethyl N-(4,5,7-trifluorobenzothiazol-2-yl)methyl-N-cyclohexylsuccinamate;
N-(4,5,7-Trifluorobenzothiazol-2-yl)methyl-N-propylsuccinamic acid;
N-(4,5,7-Trifluorobenzothiazol-2-yl)methyl-N-amylsuccinamic acid;
N-(4,5,7-Trifluorobenzothiazol-2-yl)methyl-N-hexylsuccinamic acid;
N-(4,5,7-Trifluorobenzothiazol-2-yl)methyl-N-hexadecylsuccinamic acid;
N-(4,5,7-Trifluorobenzothiazol-2-yl)methyl-N-cyclopropylmethylsuccinamic acid;
N-(4,5,7-Trifluorobenzothiazol-2-yl)methyl-N-cyclobutylsuccinamic acid;
N-(4,5,7-Trifluorobenzothiazol-2-yl)methyl-N-cyclopentylsuccinamic acid;
N-(4,5,7-Trifluorobenzothiazol-2-yl)methyl-N-methylsuccinamic acid;
N-(4,5,7-Trifluorobenzothiazol-2-yl)methyl-N-ethylsuccinamic acid;
N-(4,5,7-Trifluorobenzothiazol-2-yl)methyl-N-isopropylsuccinamic acid;
N-(4,5,7-Trifluorobenzothiazol-2-yl)methyl-N-butylsuccinamic acid;
N-(4,5,7-Trifluorobenzothiazol-2-yl)methyl-N-octylsuccinamic acid;
N-(4,5,7-Trifluorobenzothiazol-2-yl)methyl-N-allylsuccinamic acid;
Ethyl N-(4,5,7-Trifluorobenzothiazol-2-yl)methyl-N-cyclopropylsuccinamic acid and
N-(4,5,7-Trifluorobenzothiazol-2-yl)methyl-N-cyclohexylsuccinamic acid, or a pharmaceutically acceptable salt thereof.

5. A method for producing the succinamic acid compound of claim 1 or a pharmaceutically acceptable salt thereof, which comprises reacting a compound of the formula (2)

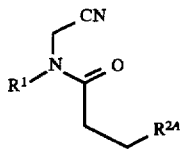 (2)

wherein $R^1$ is as defined above and $R^{2a}$ is an esterified carboxyl, or an acid addition salt thereof with 2-amino-3,4,6-trifluorothiophenol or an acid addition salt thereof, and where $R^2$ is a carboxyl, which is followed by hydrolysis of said compound, or reacting a compound of the formula (3)

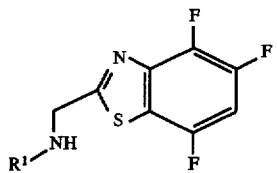 (3)

wherein $R^1$ is as defined above, with a compound of the formula (4)

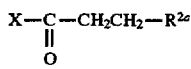 (4)

wherein $R^{2a}$ is as defined above and X is a halogen atom, or an acid addition salt thereof, and where $R^2$ is a carboxyl, which is followed by hydrolysis of said compound.

6. A pharmaceutical composition comprising the succinamic acid compound of claim 1 or a pharmaceutically acceptable salt thereof.

7. The pharmaceutical composition of claim 6, which is an aldose reductase inhibitor.

8. A method for inhibiting aldose reductase, activity, comprising administering an effective amount of the succinamic acid compound of claim 1 or a pharmaceutically acceptable salt thereof.

9. A method for the prophylaxis and/or treatment of the complications of diabetes, which comprises administering an effective amount of the succinamic acid compound of claim 1 or a pharmaceutically acceptable salt thereof.

* * * * *